(12) United States Patent
Broyer et al.

(10) Patent No.: US 7,226,537 B2
(45) Date of Patent: Jun. 5, 2007

(54) METHOD, DEVICE AND APPARATUS FOR THE WET SEPARATION OF MAGNETIC MICROPARTICLES

(75) Inventors: Patrick Broyer, Beynost (FR); Christian Jeandey, Saint Egreve (FR)

(73) Assignees: Bio Merieux, Marcy-l'Etoile (FR); Commissariat a l'Energie Atomique, Paris (FR)

( * ) Notice: Subject to any disclaimer, the term of this patent is extended or adjusted under 35 U.S.C. 154(b) by 397 days.

(21) Appl. No.: 10/480,118

(22) PCT Filed: Jun. 17, 2002

(86) PCT No.: PCT/FR02/02082

§ 371 (c)(1), (2), (4) Date: Jan. 27, 2004

(87) PCT Pub. No.: WO03/002260

PCT Pub. Date: Jan. 9, 2003

(65) Prior Publication Data

US 2004/0108253 A1 Jun. 10, 2004

(30) Foreign Application Priority Data

Jun. 27, 2001 (FR) .................................. 01 08496

(51) Int. Cl.
*B03C 1/035* (2006.01)

(52) U.S. Cl. ....................... 210/222; 210/695; 209/214; 209/232

(58) Field of Classification Search ................ 210/222, 210/695; 209/214, 232
See application file for complete search history.

(56) References Cited

U.S. PATENT DOCUMENTS 4,795,698 A 1/1989 Owen et al.
5,795,470 A * 8/1998 Wang et al. ................. 210/222
6,413,420 B1 * 7/2002 Foy et al. .................... 210/222
6,444,828 B1 9/2002 Muller et al.
6,521,431 B1 2/2003 Kiser et al.
2003/0186295 A1 10/2003 Colin et al.
2006/0078466 A1 4/2006 Colin et al.

FOREIGN PATENT DOCUMENTS

| FR | 2 813 207 A1 | 3/2002 |
| GB | 2 333 978 A | 8/1999 |
| WO | WO 98/55236 | 12/1998 |
| WO | WO 99/35500 A1 | 7/1999 |
| WO | WO 00/10978 | 3/2000 |
| WO | WO 00/78452 A1 | 12/2000 |

\* cited by examiner

*Primary Examiner*—David A. Reifsnyder
(74) *Attorney, Agent, or Firm*—Oliff & Berridge, PLC

(57) ABSTRACT

Method for the wet dynamic separation of a suspension in liquid phase, comprising microparticles comprising a magnetic material and a liquid medium in which said microparticles are in suspension, in which method:

a) the suspension is confined in a chamber having a volume defined by at least two dimensions, for example length and depth;

b) at least one plurality of elementary magnetic fields is set up, these magnetic fields being distributed in a "Halbach semi-configuration", whose respective ends facing the chamber generate a vector sum of said elementary magnetic fields, corresponding to a magnetic capture field passing through said chamber and exerting a magnetic attraction on the microparticles, and whose opposite respective ends generate no magnetic field; and c) said capture magnetic field is generated, whereby a solid phase enriched with microparticles is captured in said chamber, and a liquid phase depleted in microparticles is extracted from said chamber.

18 Claims, 4 Drawing Sheets

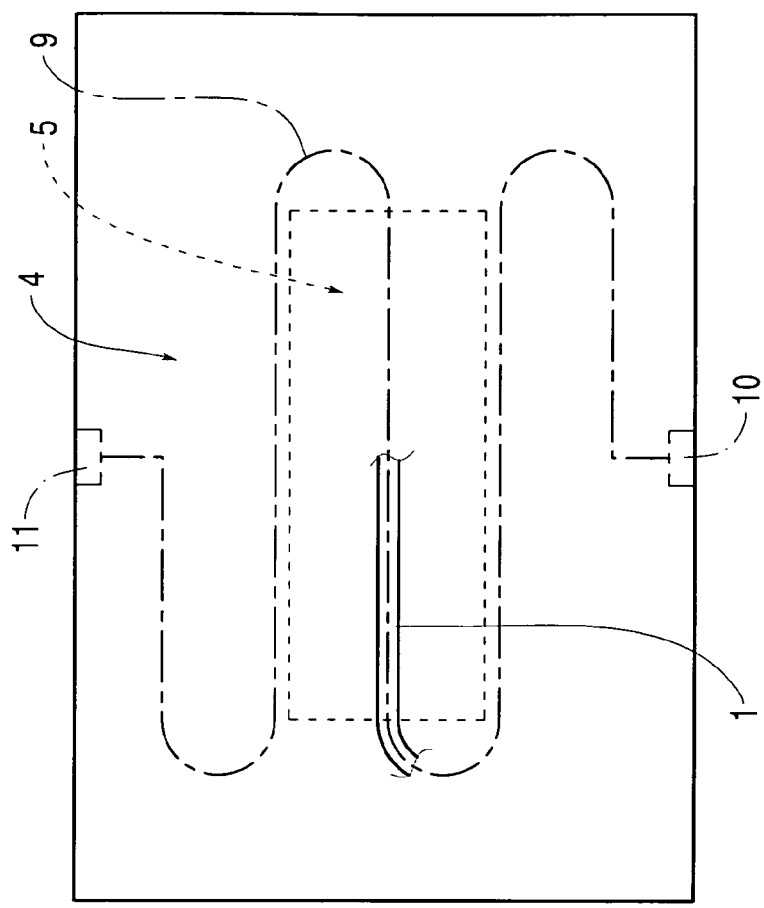
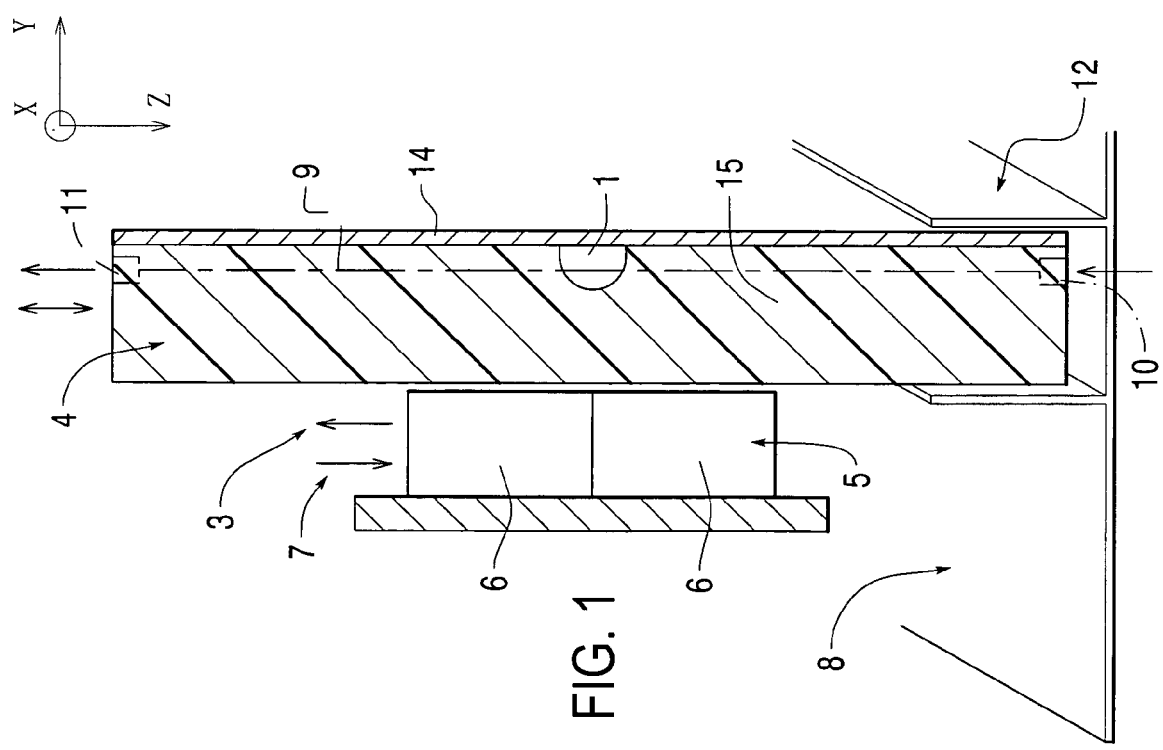

| α | n1 p1<br>n1 p2 | n2 p1<br>n2 p2 | n3 p1<br>n3 p2 | n4 p1<br>n4 p2 | n5 p1<br>n5 p2 | n6 p1<br>n6 p2 |
|---|---|---|---|---|---|---|
|  | 0<br>0 | +45<br>+45 | +90<br>+90 | +135<br>+135 | +180<br>+180 | +225<br>+225 |

METHOD, DEVICE AND APPARATUS FOR THE WET SEPARATION OF MAGNETIC MICROPARTICLES

BACKGROUND OF THE INVENTION

The present invention relates in general to wet dynamic separation of a suspension in liquid phase, comprising, on the one hand, magnetic particles, that is to say ones comprising a magnetic material, and, on the other hand, a liquid medium in which said particles are suspended.

The term "microparticles" is understood to mean particles whose size does not exceed a few microns. According to the present invention, the microparticles in question each comprise, for example, a particle made of a magnetic material and coated with a polymeric material.

The magnetic material may be of two main compositions, namely:

- a permanently magnetized material, or hard ferromagnetic material, for example hard ferrite, in which case the particles have a size of at least a few µm; or
- a material that can be magnetized in any magnetic field, or superparamagnetic material, in which case the particles have a size of at most a few tens of nm.

DESCRIPTION OF THE PRIOR ART

Superparamagnetic microparticles have been described in various documents, including U.S. Pat. No. 4,795,698, and these microparticles are available from various manufacturers and/or under various trade names, such as SERADYN, IMMUNICON, etc.

Moreover, according to Patent Application WO-A-99/35500, of which one of the Applicants is the proprietor, heat-sensitive magnetic particles are known and these can also be used.

When these microparticles are functionalized, that is to say linked to reactants or entities of the biological, biochemical or chemical type, or of any nature, at one or more external sites on the same microparticle, the functionalized microparticles thus obtained are of great interest as they make it possible in particular to carry out automated determinations, especially biological assays and immunological assays.

Preferably, the reactants are then entities of the type including antigens, antibodies, antibody fragments, haptens, vitamins, proteins, polypeptides, peptides, receptors, enzymes, nucleic acids, oligonucleotides, polynucleotides, etc.

The reactants are in turn capable of reacting with biological entities of interest.

In one application of the assay type, in which the microparticles are brought into contact with a specimen containing biological entities of interest, it is then necessary, at one moment or another in said assay, to separate the suspension of microparticles in liquid phase into, on the one hand, a solid phase enriched with microparticles, and therefore with biological entities of interest, and, on the other hand, a liquid phase depleted in microparticles.

Owing to the magnetic nature of the microparticles, such a phase separation is carried out using magnetic means.

For this purpose, according to the document U.S. Pat. No. 5,795,470 (cf. FIG. 13):

a) the suspension is confined in a chamber, the volume of which is defined by at least two dimensions or directions, namely a reference dimension, corresponding to the direction of flow of a specimen of the suspension, and a dimension transverse or perpendicular to the reference dimension, for example depth;

b) a capture magnetic field is set up across said chamber, said field resulting from the vector sum of two parallel and spaced-apart pluralities or rows of alternating elementary magnetic fields lying on either side of the chamber along the transverse dimension, said elementary magnetic fields, each parallel to the transverse dimension, being distributed in each row along a dimension perpendicular to the reference and transverse dimensions; the capture magnetic field thus obtained exerts a magnetic attraction on the microparticles, a major component of which magnetic attraction, for example the entire magnetic attraction, is directed along the transverse dimension against the respective two faces of the vessel on either side of the transverse dimension;

c) the capture magnetic field is generated by placing the chamber between the two rows of elementary magnetic fields, whereby a solid phase enriched with microparticles is captured in the chamber, either dynamically or statically, and a liquid phase depleted in microparticles is extracted from this chamber; and d) by moving the chamber away from the two rows of elementary magnetic fields, the solid phase enriched with microparticles is released, for example by means of a liquid releasing medium, or a liquid for putting them back into suspension.

According to the solution described above, the elementary magnetic fields generate, by their vector sum, not only the capture magnetic field but also stray magnetic fields in the region surrounding the chamber for separating the suspension of microparticles. Consequently, on the one hand, this technique can be put into practice only on one and the same isolated chamber and, on the other hand, this technique is excluded from any automated and grouped use, for example of analytical cards placed vertically on their edge and placed parallel to one another side by side, a short distance (less than 3 cm for example) apart.

The present invention aims to remedy this drawback. In particular, the subject of the present invention is a separation technique for confining the capture magnetic field practically within the chamber for separating the suspension of microparticles, irrespective of the dimensions of said chamber within certain limits.

SUMMARY OF THE INVENTION

The present invention relates to a method of the kind defined above, in which:

a) the suspension is confined in a chamber having a volume defined by at least two dimensions, for example length and depth;

b) at least one plurality of elementary magnetic fields is set up, these magnetic fields being distributed in a "Halbach semi-configuration", whose respective ends facing the chamber generate a vector sum of said elementary magnetic fields, corresponding to a magnetic capture field passing through said chamber and exerting a magnetic attraction on the microparticles, and whose opposite respective ends generate no magnetic field; and c) said capture magnetic field is generated, whereby a solid phase enriched with microparticles is captured in said chamber, and a liquid phase depleted in microparticles is extracted from said chamber.

Correspondingly, the invention relates to a device comprising:

a) a container in which a chamber is formed, having a volume defined by at least two dimensions, for example length and depth, said chamber being suitable for confining a specimen of said suspension;

b) magnetic means external to the container, consisting of at least one arrangement formed by at least one plurality of elementary magnets, said magnets being distributed in a "Halbach semi-configuration", whose respective faces facing the chamber generate a vector sum of elementary magnetic fields, corresponding to a capture magnetic field passing through said chamber, and whose opposite respective faces generate no magnetic field; and c) means for generating said capture magnetic field.

The expression "Halbach semi-configuration" is understood to mean any configuration in which the elementary magnetic fields (or elementary magnets) are distributed and aligned along the same direction, are all parallel or coincident with a plane of rotation, have respective directions intersecting at a common center (O) lying between said plane of rotation, and have respective senses, projected onto said plane of rotation, which are obtained, from a starting direction passing through the common center, with an angular pitch, corresponding to the switching from one elementary magnetic field to the adjacent other one, along the direction of alignment of said fields, whereby the vector sum of said magnetic fields corresponds to a resultant magnetic field (cf. Klaus Halbach, Nuclear Instruments and Methods, Vol. 169, pp 1–7, 1980 and Nuclear Instruments and Methods, Vol. 187, pp 109–117, 1981).

The present invention also presents the following variants, relating to the wet dynamic separation method:

after phase c), said capture magnetic field is removed, whereby said solid phase enriched with microparticles is released, for example by means of a liquid releasing medium;

the elementary magnetic fields are aligned along one dimension of the chamber, for example the length, and the plurality of said elementary magnetic fields are parallel or coincident with a plane known as the plane of rotation of said fields, for example containing said length;

a multiplicity of elementary magnetic fields is distributed in a plurality of rows, distributed along a third dimension, for example perpendicular to at least one of the two dimensions of the chamber.

The present invention also presents the following variants relating to the wet separation device:

it includes means for generating and then removing the capture magnetic field;

the container has a flat shape and is obtained by assembly of a plate, in which the chamber is made, and of a plastic film attached to the plate, and the magnetic means are placed either on the plate side or on the film side;

the elementary magnets are placed along an alignment direction so as to be contiguous with one another or to be separated from one another;

the elementary magnets are aligned along one dimension of the chamber, for example the length, and placed in such a way that the plurality of elementary magnetic fields, generated by said respective elementary magnets, are parallel to or coincident with a plane known as the plane of rotation of said fields, for example containing said length;

the multiplicity of elementary magnets is distributed in a plurality of contiguous or spaced-apart rows distributed along a third dimension, for example perpendicular to at least one of the dimensions of the chamber.

The solution according to the present invention offers the following key advantages, demonstrated in particular by the experimental protocol described below.

Firstly, the solid phase enriched with microparticles is separated relatively quickly, for example in less than one minute, this constituting an appreciable advantage when conducting an automated biotest, making it possible for example to increase the speed of the automatic analyzer by means of which the biological entity of interest (for example) is determined.

Secondly, by confining the capture magnetic field it is possible to concentrate the latter, maximize its gradient and ensure good retention of the aforementioned solid phase in the separating chamber, while withstanding the hydrodynamic stresses of the liquids or fluids circulating within the separating chamber. In this regard, the loss of microparticles may be less than 1% by weight.

Thirdly, the virtual absence of a stray magnetic field in the separating chamber, when the capture magnetic field is removed, allows the microparticles to be easily put back into a homogenous suspension.

According to the abovementioned prior art, the chamber containing the microparticles can move, whereas, according to the invention, the chamber can be stationary and the magnetic means can move correspondingly.

Fourthly, according to the invention, the magnetic energy is concentrated on only one side of the magnetic means, thereby dispensing with the need for any shielding on the other side. This advantage is essential in the case of a device in which analytical cards are placed side by side a short distance apart.

Fifthly, the location and the distribution of the microparticles within the chamber (for example in the bottom of a channel of an analytical card) is better defined and therefore simplifies the management of the pressure cycles during the step of putting the microparticles back into suspension in an automatic assay machine.

With regard to the analytical cards that will be considered below, in particular those suitable for use in an automatic machine, reference may be made in particular to French Patent Application FR 00/10978 and to International Application WO-A-00/78452, of which one of the Applicants is the proprietor.

BRIEF DESCRIPTION OF THE DRAWINGS

The present invention will now be described with reference to the appended drawing, in which:

FIG. 1 shows, schematically, and seen in perspective, an apparatus according to the invention that incorporates a device according to the invention;

FIG. 2 shows, on a smaller scale, the device according to the invention, in a view from the front, and corresponding to the device shown in FIG. 1;

DESCRIPTION OF THE PREFERRED EMBODIMENTS

Figures 3, 4:
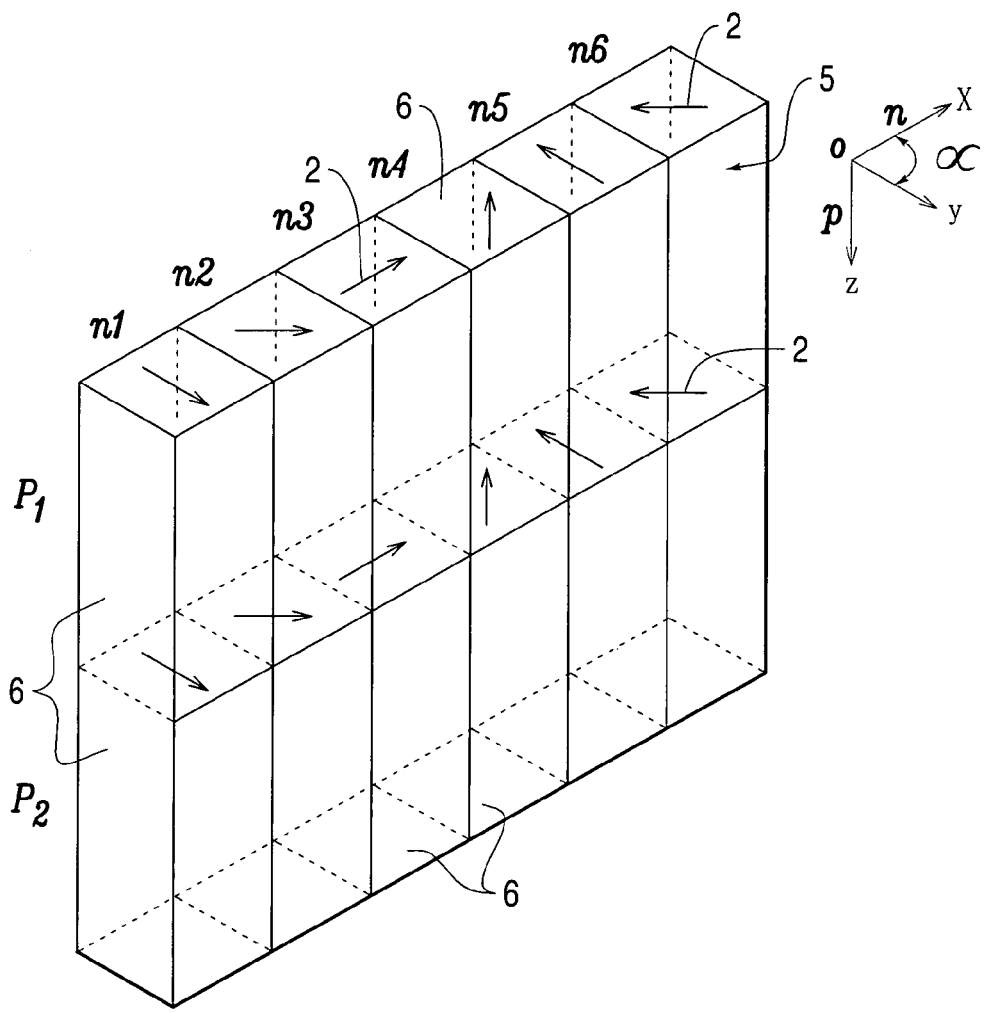
FIG. 3 shows schematically, and seen in perspective, the magnetic means of a device according to the invention.
FIG. 4 is a table showing, as an example, the step-by-step angular rotation of the magnetic fields generated by the elementary magnets belonging to the magnetic means shown in FIG. 3.

According to FIG. 1, an apparatus 8 according to the invention comprises:

one or more containers 4 for example consumable containers of the card type, each comprising a circuit 9 for circulation of a suspension in liquid phase, as defined above, that is to say one comprising magnetic microparticles and a liquid medium in which the latter are suspended; belonging to this container, and, incorporated into the circuit 9, is a reference or separating chamber 1, which will be discussed below in order to explain the invention, and which chamber is connected, via the circuit 9, to at least one inlet 10 and one outlet 11, said inlet and outlet being placed within the container 4;

a support 12 for positioning, for example in a removable manner, the container or containers 4 in such a way that the chamber 1, for example belonging to a circuit for circulation of the suspension in liquid phase, is aligned with or parallel to a reference direction Ox, or length direction, which will be explained below with reference to FIG. 3; and means 7 for generating and then removing a capture magnetic field, introduced and explained with reference to FIGS. 3 and 4, consisting of means 7 (shown schematically in FIG. 1) for moving magnetic means 5 parallel to a plane perpendicular to a transverse direction Oy, for example the depth direction (cf. FIG. 3), form an active position, in which the capture magnetic field passes through the chamber 1, to an inactive position, in which the capture magnetic field is placed away from the chamber 1.

In practice, and as a person skilled in the art knows, the container 4, or consumable of the card type, has a flat parallelepipedal shape and is obtained by assembly, on the one hand, of a plastic sheet 15, in which both the circulation circuit 9 and a chamber or channel 1 are obtained, for example by molding, these being placed on at least one side of the aforementioned sheet, and, on the other hand, of a plastic film 14 attached to the sheet 15, for example by adhesive bonding; this film therefore closes off the entire circuit 9.

The support 12 involved here is, for example, formed by the bottom of a rack in which slots or other removable retention means are provided, in order to accommodate the various containers 4, vertically and on their respective edges, in the position exemplified in FIG. 1, that is to say parallel to the xOz plane (cf. FIG. 3) while keeping them spaced apart.

Such a support or rack 12 forms part of, for example, an automatic analyzer, which also includes the means 7 for moving, in vertical translation and parallel to the container 4 (in their position shown in FIG. 1), the magnetic means 5 that are assigned respectively to the various containers 4, and in succession into their active and inactive positions defined above. These means 7 are formed by any means of the prior art known to those skilled in the art for making said magnetic means 5 undergo a reversible translational movement.

Although not shown, the apparatus described above includes means for circulating liquids or other fluids in the circuit 9 of the various containers 4, for example pumps or other suction and/or delivery means, and for doing so via at least the inlet 10 and/or the outlet 11 of the circuit 9.

Figure 5:
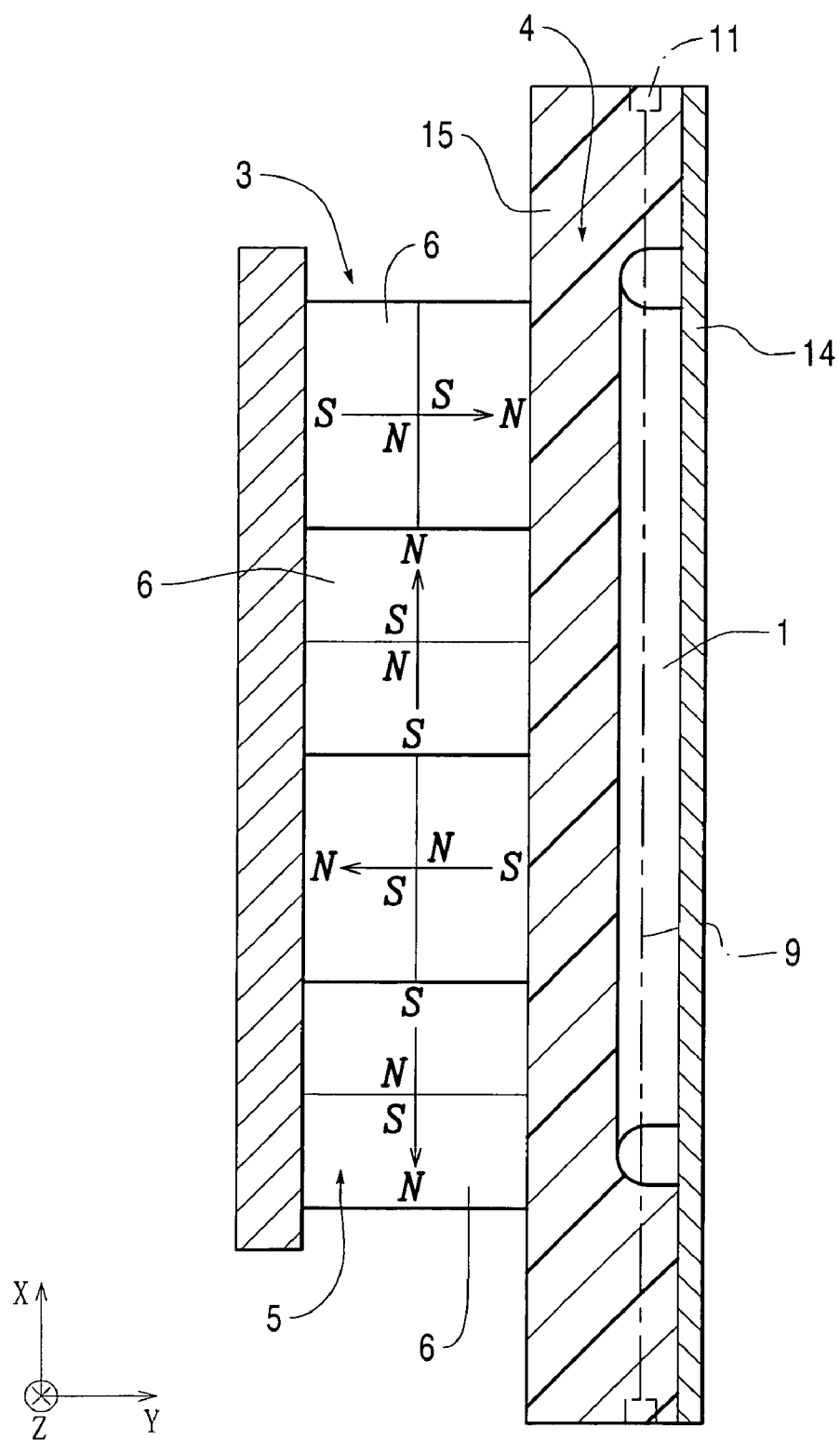
FIG. 5 shows, in the same way as in FIG. 1, an experimental setup for characterizing the performance characteristics obtained with a device according to the invention.

Although again not shown, the aforementioned circulation means are designed and/or programmed to carry out, in the chamber 1, which will be explained below, the following steps, namely, in succession:

when the magnetic means 5 shown for example in FIGS. 1 and 5 are in the active position, the specimen, for example a biological specimen, is made to circulate in and through the chamber 1 in order:

to separate, in said chamber, a solid phase or fraction enriched with microparticles, and therefore with biological entities of interest, initially present in said specimen, having been captured by the reactants or entities carried by the microparticles, and to reject, from the same chamber, for example as a supernatant, a liquid phase or fraction depleted in microparticles, and therefore in biological entities of interest;

optionally, again when the magnetic means 5 are in the same active position, a liquid washing phase circulates in the chamber 1, in contact with the solid phase enriched with microparticles, and therefore with biological entities of interest; and optionally, either when the magnetic means 5 are in the active position, the solid phase enriched with microparticles, and therefore with biological entities of interest, is freed and then released, for example by circulation of a liquid phase for putting the microparticles back into suspension, or when the same magnetic means 5 are in the active position, the biological entities of interest are separated from the microparticles and released into a liquid capture phase, whereas the microparticles remain trapped by the magnetic means 5; in the latter case, the biological entities released can then be moved away, for example by the abovementioned circulation means, in order to carry out other operations such as transfers, reactions, etc.

Such is the technical environment into which a device according to the invention for implementing the method according to the same invention falls.

As shown in FIG. 1, a device 3 according to the invention, for wet dynamic separation of the abovementioned suspension, comprises or combines:

a) the container 4, which in practice may be disposable, in which the chamber 1 is provided, knowing that in general the volume of this chamber is defined by at least two dimensions, namely a reference direction Ox, for example the length direction, along which the chamber 1 or channel is arranged, and a transverse direction Oy, or one that is perpendicular to the aforementioned reference direction (cf. the coordinates system of FIG. 3), for example the depth of the chamber 1, this chamber 1 being in general suitable for confining a specimen of the suspension for the purpose of its elementary separation described below;

b) the magnetic means 5, placed on the outside of the container 4, consisting, as shown in figure 3, in an arrangement formed by two pluralities (2n) and (2p) of elementary magnets 6, distributed along a predetermined direction, in this case Ox, these two pluralities being superposed along another direction Oz, or transverse direction, in such a way as to generate, by the vector sum of the elementary magnetic fields 2, generated by said elementary magnets 6 respectively, a capture magnetic field that passes through the chamber 1 and exerts a magnetic attraction on the microparticles, a major component of which attraction, for example the entire attraction, is directed along the transverse direction Oz; and c) the means 7 (shown schematically in FIG. 1) for generating the capture magnetic field and then for removing it, whereby the solid phase enriched with microparticles is captured in the chamber 1 and then released.

According to the present invention, as may be seen with reference to FIG. 3 and to the table in FIG. 4, the elementary magnets 6 are aligned along the reference direction Ox and arranged in such a way as to generate respective elementary magnetic fields 2 that are parallel to or coincident with a plane known as the plane of rotation, in this case xOy. The rotation of the elementary magnetic fields 2, corresponding to the switch from one elementary magnet 6 to an adjacent other one, is a step-by-step rotation, in the same sense, and at constant angular pitch. A capture magnetic field, resulting from the vector sum of said elementary magnetic fields 2, is thereby generated.

The elementary magnets 6 are placed as shown in FIG. 3 so as to be contiguous with one another, but they may also be distributed and separated from one another along the reference direction Ox.

Each elementary magnet 6 is of prismatic shape, for example with a square base (as shown in FIG. 3), a hexagonal base or a circular base.

According to the invention, for a channel of direction Ox, the elementary magnets 6 are aligned along this direction Ox, and the plane of rotation of the elementary magnetic fields contains the axis Ox.

The device, described above in terms of its principals, is used to carry out a wet dynamic separation step on a suspension of magnetic microparticles in liquid phase, as follows:

a) the suspension is confined in the chamber 1, for example using the circulation means provided in the apparatus described above;

b) using the magnets 6, at least one plurality or multiplicity of elementary magnetic fields 2, distributed along a predetermined direction (Ox or Oz), relative to the reference Ox and transverse direction Oy, are produced in such a way as to generate the capture magnetic field, by the vector sum of said elementary magnetic fields, which passes through the chamber 1 and exerts a magnetic attraction on the microparticles to be separated, a major component of which attraction, for example the entire attraction, is directed along the transverse direction Oy;

c) the capture magnetic field is generated when the magnetic means 5 are in the active position, whereby the solid phase enriched with microparticles is captured in the chamber 1 and, at the same time, the liquid phase depleted in microparticles is removed from said chamber; and d) the capture magnetic field is removed when the magnetic means 5 are in the inactive position, whereby the solid phase enriched with microparticles is released, for example by means of a releasing liquid or liquid for putting them back into suspension.

During phase b), the magnetic separation may also be carried out dynamically, so as to limit the number of elementary magnets 6 aligned along the direction Ox, if the length of the liquid segment in the chamber 1 is sufficient compared to the length occupied by the magnets 6, by making scans (to and fro) of said liquid segment in front of the set of magnets.

EXAMPLE 1

Figure 6:
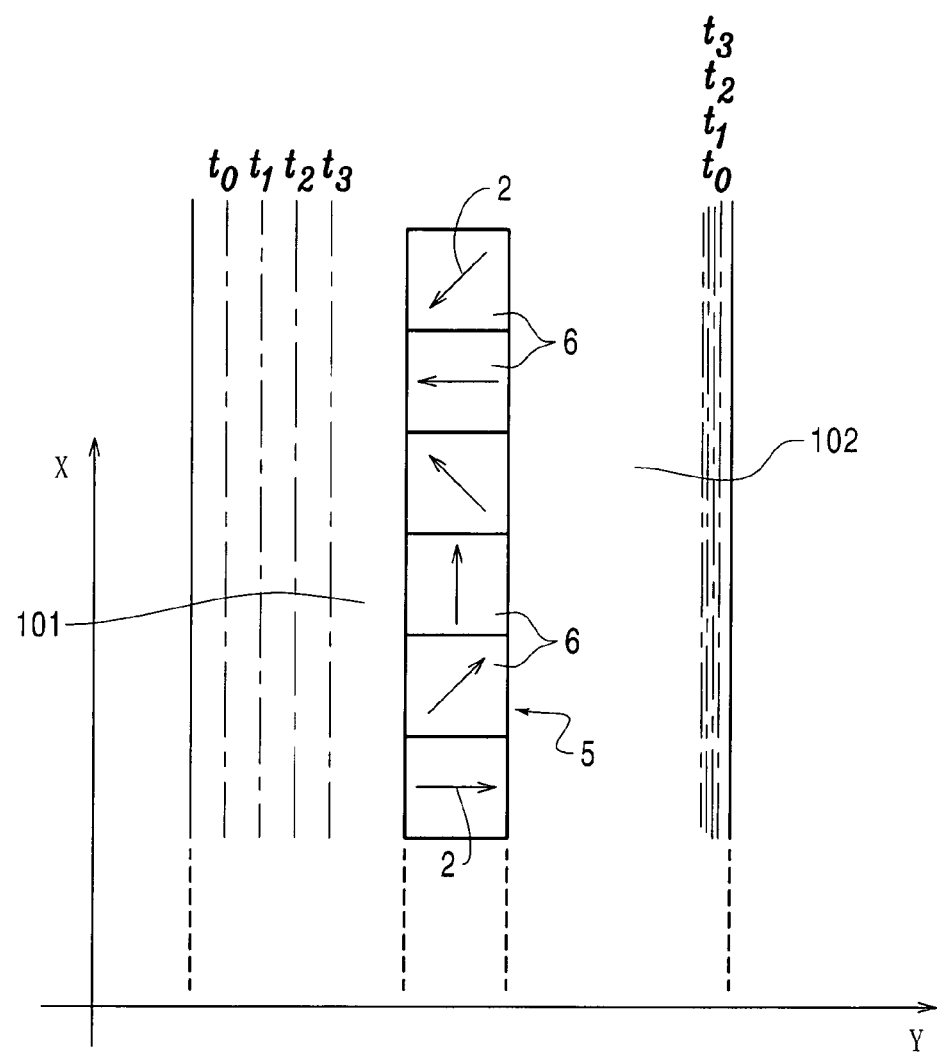
FIG. 6 shows schematically a device according to the invention, in accordance with that shown with reference to FIGS. 1 and 3, in which two chambers are placed on either side of the magnetization means, and for which the change in position of the microparticles in the presence of the capture magnetic field has been shown.

According to FIG. 6, two chambers 101 and 102 are placed on either side of the magnetic means 5, and the same suspension of microparticles is present in each of said chambers. In the presence of the capture magnetic field, the microparticles in the chamber 101 migrate over time as a front moving toward the magnetic means 5, whereas the microparticles in the chamber 102 stagnate in a front away from the magnetic means 5.

The number of elementary magnets 6 aligned along the reference direction, for example Ox in FIGS. 1 and 3, is not a restricting parameter. This number has simply to be tailored to the required magnetic field and to the required size.

For example, in FIG. 5 there are four elementary magnets 6 because the rotation defined above has a 90° pitch, so that with four magnets one revolution is completed.

In FIG. 3, there are six elementary magnets; it is possible to use eight of them in order for there to be one complete rotation of the elementary magnetic fields 2, with a rotation pitch of 45°.

Figure 7:
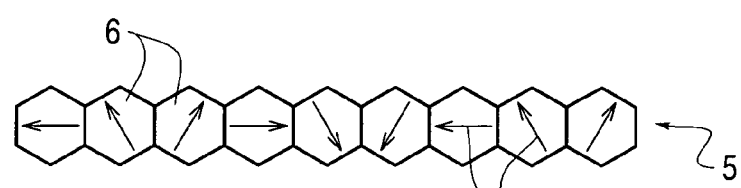
FIGS. 7 and 8 show two other arrangements or configurations respectively, with elementary magnets having hexagonal and circular cross sections respectively, each of these arrangements being shown seen from above, in the manner of FIG. 6.

The arrangement shown in FIG. 7, consisting for example of nine elementary magnets 6 with a rotation pitch of 60°, makes it possible to optimize the size and the cost of the elementary magnets, since there is no loss of magnetic material at the cutting stage.

Figure 8:
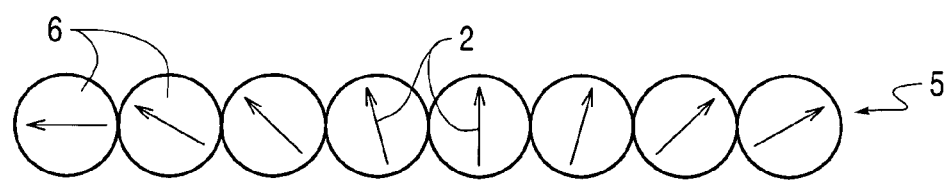

The arrangement shown in FIG. 8, consisting for example of eight elementary magnets 6, with any rotation pitch, is suitable, but when the rotation pitch decreases, the range of the capture magnetic field increases but the amount of space occupied is greater.

EXAMPLE 2

An arrangement according to the invention was obtained as in FIG. 5, with elementary magnets 2 of cubic shape (4×4×4 millimeters), such as those available form Binder Magnetic under the brand name NEUU.

The magnetic means 5 thus obtained were placed as shown in FIGS. 1 and 2 relative to a reference channel or chamber 1.

The concentration of microparticles was measured, on any effluent, that is to say liquid stream leaving the container or card 4 via the outlet 11, by means of a spectrophotometer for measuring the optical density at 875 nm.

The circulation protocol described above was used with microparticles of the SERADYN brand, with an initial suspension of 0.25 µg/µl, the injected volume being 50 µl; 25 µl of supernatant were recovered via the outlet 11 and the optical density thereof was measured.

The liquid displacements were obtained in the container or card 4 by means of a syringe connected to the inlet 10.

The magnetic separation time, on the one hand, and the optical density, obtained after dilution to $\frac{1}{16}$, on the other hand, were measured firstly with conventional magnetic means, consisting of a simple magnet and then with the configuration of the magnetic means which is shown in FIG. 5.

The results obtained are given in the table below.

| Magnetic Separation Time | OD Measured at 875 nm with 1/16 dilution | |
|---|---|---|
| | Simple Magnet Configuration | Configuration According to FIG. 5 |
| 15 sec | 0.076 | 0.012 |
| 30 sec | 0.013 | 0.0089 |
| 45 sec | 0.029 | 0.0095 |
| 1 min | 0.012 | 0.003 |

A few measurements carried out with a much lower microparticle concentration, for example 1 µg/µl, showed an even more pronounced difference between the optical density values obtained by conventional magnetic means and by magnetic means according to the invention, respectively.

By virtue of the arrangement in FIG. 5, it may be seen visibly that the supernatant rapidly becomes clear, within a time of 1 minute. A less diffuse microparticle distribution is also observed in the channel or chamber 1 with the arrangement according to FIG. 5 than with a conventional arrangement.

It should be noted that the OD value at 1 minute, obtained with a particularly simple arrangement, was the same as that obtained with the arrangement shown in FIG. 5 after only 12 seconds.

The arrangement shown in FIG. 5 makes it possible to confine the microparticles in a better defined region corresponding in practice to only the separating channel or chamber 1.

The invention claimed is:

1. A method for the wet dynamic separation of a suspension in liquid phase, comprising microparticles comprising a magnetic material and a liquid medium in which said microparticles are in suspension, in which method:
   a) the suspension is confined in a chamber having a volume defined by at least a first dimension and a second dimention;
   b) at least one plurality of elementary magnetic fields is set up, these magnetic fields being distributed in a "Halbach semi-configuration", whose respective ends facing the chamber generate a vector sum of said elementary magnetic fields, corresponding to a magnetic capture field passing through said chamber and exerting a magnetic attraction on the microparticles, and whose opposite respective ends generate no magnetic field, wherein a multiplicity of elementary magnetic fields is distributed in a plurality of rows along a third dimension wherein said third dimension is perpendicular to at least said first dimension or said second dimension of the chamber; and
   c) said capture magnetic field is generated, whereby a solid phase enriched with microparticles is captured in said chamber, and a liquid phase depleted in microparticles is extracted from said chamber.

2. The method as claimed in claim 1, wherein, after phase c), said capture magnetic field is removed, whereby said solid phase enriched with microparticles is released.

3. The method as claimed in claim 1, wherein the elementary magnetic fields are aligned along a first dimension of the chamber and the plurality of said elementary magnetic fields are parallel or coincident with a plane known as the plane of rotation of said fields, the plane containing said first dimension of the chamber.

4. A device for the wet dynamic separation of a suspension in liquid phase, comprising microparticles comprising a magnetic material and a liquid medium in which said microparticles are in suspension, said device comprising:
   a) a container in which a chamber is formed, having a volume defined by at least a first dimension and a second dimension, said chamber being suitable for confining a specimen of said suspension;
   b) magnetic means external to the container, consisting of at least one arrangement formed by at least one plurality of elementary magnets, said magnets being distributed in a "Halbach semi-configuration", whose respective faces facing the chamber generate a vector sum of elementary magnetic fields, corresponding to a capture magnetic field passing through said chamber, and whose opposite respective faces generate no magnetic field; and
   c) means for generating said capture magnetic field;
   wherein:
   the elementary magnets are aligned along a first dimension of the chamber and placed in such a way that the plurality of elementary magnetic fields, generated by said respective elementary magnets, are parallel to or coincident with a plane known as the plane of rotation of said fields, the plane containing said first dimension of the chamber.

5. The device as claimed in claim 4, which includes means for removing the capture magnetic field.

6. An apparatus for the use of a device as claimed in claim 5, wherein:
   the container comprises a circuit for the circulation of at least one suspension in liquid phase, to which said chamber belongs, and which is connected to at least one inlet and one outlet;
   a support for positioning said container in such a way that the chamber is aligned with or is parallel to the direction of the capture magnetic field; and
   optionally, means for generating the capture magnetic field and then for removing it, consisting of means for moving the magnetic means from an active position, in which the capture magnetic field is generated across said chamber, to an inactive position, in which the capture magnetic field is placed away from said chamber.

7. The device as claimed in claim 4, whereby the container has a flat shape and is obtained by assembly of a plate, in which the chamber is made, and of a plastic film attached to the plate, wherein the magnetic means are placed either on the plate side or on the film side.

8. An apparatus for the use of a device as claimed in claim 7, wherein:
   the container comprises a circuit for the circulation of at least one suspension in liquid phase, to which said chamber belongs, and which is connected to at least one inlet and one outlet;
   a support for positioning said container in such a way that the chamber is aligned with or is parallel to the direction of the capture magnetic field; and
   optionally, means for generating the capture magnetic field and then for removing it, consisting of means for moving the magnetic means from an active position, in which the capture magnetic field is generated across said chamber, to an inactive position, in which the capture magnetic field is placed away from said chamber.

9. The device as claimed in claim 4, wherein the elementary magnets are placed along an alignment direction so as to be contiguous with one another or to be separated from one another.

10. An apparatus for the use of a device as claimed in claim 9, wherein:
- the container comprises a circuit for the circulation of at least one suspension in liquid phase, to which said chamber belongs, and which is connected to at least one inlet and one outlet;
- a support for positioning said container in such a way that the chamber is aligned with or is parallel to the direction of the capture magnetic field; and
- optionally, means for generating the capture magnetic field and then for removing it, consisting of means for moving the magnetic means from an active position, in which the capture magnetic field is generated across said chamber, to an inactive position, in which the capture magnetic field is placed away from said chamber.

11. The device as claimed in claim 4, wherein each elementary magnet has a prismatic shape.

12. An apparatus for the use of a device as claimed in claim 11, wherein:
- the container comprises a circuit for the circulation of at least one suspension in liquid phase, to which said chamber belongs, and which is connected to at least one inlet and one outlet;
- a support for positioning said container in such a way that the chamber is aligned with or is parallel to the direction of the capture magnetic field; and
- optionally, means for generating the capture magnetic field and then for removing it, consisting of means for moving the magnetic means from an active position, in which the capture magnetic field is generated across said chamber, to an inactive position, in which the capture magnetic field is placed away from said chamber.

13. The device as claimed in claim 4, wherein the multiplicity of elementary magnets is distributed in a plurality of contiguous or spaced-apart rows distributed along a third dimension, wherein said third dimension is perpendicular to at least said first dimension or said second dimension of the chamber.

14. An apparatus for the use of a device as claimed in claim 13, wherein:
- the container comprises a circuit for the circulation of at least one suspension in liquid phase, to which said chamber belongs, and which is connected to at least one inlet and one outlet;
- a support for positioning said container in such a way that the chamber is aligned with or is parallel to the direction of the capture magnetic field; and
- optionally, means for generating the capture magnetic field and then for removing it, consisting of means for moving the magnetic means from an active position, in which the capture magnetic field is generated across said chamber, to an inactive position, in which the capture magnetic field is placed away from said chamber.

15. An apparatus for the use of a device as claimed in claim 4, wherein:
- the container comprises a circuit for the circulation of at least one suspension in liquid phase, to which said chamber belongs, and which is connected to at least one inlet and one outlet;
- a support for positioning said container in such a way that the chamber is aligned with or is parallel to the direction of the capture magnetic field; and
- optionally, means for generating the capture magnetic field and then for removing it, consisting of means for moving the magnetic means from an active position, in which the capture magnetic field is generated across said chamber, to an inactive position, in which the capture magnetic field is placed away from said chamber.

16. The apparatus as claimed in claim 15, which includes means for circulating liquids in the circuit of the container via the inlet and/or the outlet of said circuit.

17. The apparatus as claimed in claim 16, wherein the circulation means are designed and/or programmed to carry out in the chamber, in succession, the following steps:
- when the magnetic means are in the active position, the suspension is made to circulate in the chamber in order to separate, in the latter, the solid phase enriched with microparticles and to discharge from said chamber the liquid phase depleted in microparticles;
- optionally, when the magnetic means are in the active position, a liquid washing phase circulates in the chamber in contact with the solid phase enriched with microparticles; and
- optionally, when the magnetic means are in the inactive position, the solid phase enriched with microparticles is released by circulating a liquid phase for putting these microparticles back into suspension.

18. An apparatus for the use of a device as claimed in claim 4, wherein:
- the container comprises a circuit for the circulation of at least one suspension in liquid phase, to which said chamber belongs, and which is connected to at least one inlet and one outlet;
- a support for positioning said container in such a way that the chamber is aligned with or is parallel to the direction of the capture magnetic field; and
- optionally, means for generating the capture magnetic field and then for removing it, consisting of means for moving the magnetic means from an active position, in which the capture magnetic field is generated across said chamber, to an inactive position, in which the capture magnetic field is placed away from said chamber.

* * * * *